US012685847B2

(12) United States Patent
Davis et al.

(10) Patent No.: US 12,685,847 B2
(45) Date of Patent: Jul. 21, 2026

(54) HIGH PRESSURE INFLATION DEVICE

(71) Applicant: Merit Medical Systems, Inc., South Jordan, UT (US)

(72) Inventors: Jon Davis, Sandy, UT (US); Dan O'Neill, Salt Lake City, UT (US); Taylor Beard, West Jordan, UT (US); Michael Dean Haslam, Sandy, UT (US); Richard P. Jenkins, Bluffdale, UT (US); Dallin Romney, South Jordan, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 384 days.

(21) Appl. No.: 18/481,067

(22) Filed: Oct. 4, 2023

(65) Prior Publication Data

US 2024/0115839 A1 Apr. 11, 2024

Related U.S. Application Data

(60) Provisional application No. 63/378,429, filed on Oct. 5, 2022.

(51) Int. Cl.
*A61M 25/10* (2013.01)

(52) U.S. Cl.
CPC .................. *A61M 25/10182* (2013.11); *A61M 25/10184* (2013.11)

(58) Field of Classification Search
CPC .................. A61M 25/10182; A61M 25/10184
See application file for complete search history.

(56) References Cited

U.S. PATENT DOCUMENTS

| | | | |
|---|---|---|---|
| 3,495,494 A | 2/1970 | Scott | |
| 4,919,121 A | 4/1990 | Rydell et al. | |
| 5,011,476 A | 4/1991 | Foster | |
| 5,047,015 A * | 9/1991 | Foote ..................... | A61M 3/00 604/99.01 |
| 5,057,078 A | 10/1991 | Foote et al. | |
| 5,163,904 A | 11/1992 | Lampropoulos et al. | |
| 5,168,757 A | 12/1992 | Rabenau et al. | |
| 5,209,732 A | 5/1993 | Lampropoulos et al. | |
| 5,279,563 A | 1/1994 | Brucker et al. | |
| 5,306,248 A | 4/1994 | Barrington | |
| 5,336,183 A | 8/1994 | Greelis et al. | |

(Continued)

FOREIGN PATENT DOCUMENTS

| | | |
|---|---|---|
| CA | 2049067 | 9/1998 |
| EP | 0565045 | 10/1993 |

(Continued)

OTHER PUBLICATIONS

European Examination Report dated Mar. 28, 2019 for EP14836509. 1.

(Continued)

*Primary Examiner* — Dung T Ulsh
(74) *Attorney, Agent, or Firm* — Dorsey & Whitney LLP

(57) ABSTRACT

Devices used to pressurize, depressurize, or otherwise displace fluid are disclosed. The devices may be configured to displace fluid in order to inflate or deflate a medical device, such as a balloon. The devices further include features and mechanisms for limiting pressure generation so as to avoid damage due to overpressurization.

20 Claims, 10 Drawing Sheets

(56) References Cited

U.S. PATENT DOCUMENTS

| | | | |
|---|---|---|---|
| 5,425,713 | A | 6/1995 | Taylor et al. |
| 5,453,091 | A | 9/1995 | Taylor et al. |
| 5,507,727 | A | 4/1996 | Crainich |
| 5,554,132 | A | 9/1996 | Straits et al. |
| 5,571,133 | A | 11/1996 | Yoon |
| D376,357 | S | 12/1996 | Ferland |
| 5,609,604 | A | 3/1997 | Schwemberger |
| 5,674,237 | A | 10/1997 | Ott |
| 5,713,242 | A | 2/1998 | Kanner et al. |
| D401,324 | S | 11/1998 | Hjertman et al. |
| 5,921,968 | A | 7/1999 | Lampropoulos et al. |
| 6,050,972 | A | 4/2000 | Zadno-Azizi et al. |
| 6,106,496 | A | 8/2000 | Arnissolle |
| 6,221,091 | B1 | 4/2001 | Khosravi |
| 6,254,642 | B1 | 7/2001 | Taylor |
| 6,264,700 | B1 | 7/2001 | Kilcoyne et al. |
| D489,456 | S | 5/2004 | Groenke et al. |
| 6,796,959 | B2 | 9/2004 | Davis et al. |
| 6,936,034 | B2 | 8/2005 | Watkins |
| D545,429 | S | 6/2007 | Hayes |
| D547,841 | S | 7/2007 | Ziemann et al. |
| 7,291,132 | B2 | 11/2007 | Deruntz et al. |
| 7,351,223 | B2 | 4/2008 | Call |
| 7,530,970 | B2 | 5/2009 | McArthur et al. |
| 7,695,446 | B2 | 4/2010 | Levine et al. |
| 7,892,202 | B2 | 2/2011 | Lampropoulos et al. |
| 8,118,776 | B2 | 2/2012 | Lampropoulos et al. |
| 8,137,307 | B2 | 3/2012 | Tennican et al. |
| D661,389 | S | 6/2012 | Morgan et al. |
| D667,950 | S | 9/2012 | Hyun et al. |
| D683,452 | S | 5/2013 | Davies |
| 8,500,821 | B2 | 8/2013 | Sobrino-Serrano et al. |
| 8,506,572 | B2 | 8/2013 | Evans et al. |
| D690,417 | S | 9/2013 | Solomon |
| 8,545,442 | B2 | 10/2013 | Lampropoulos et al. |
| D710,496 | S | 8/2014 | Stevens et al. |
| D726,311 | S | 4/2015 | Lampropoulos et al. |
| D731,054 | S | 6/2015 | Lampropoulos et al. |
| 9,452,279 | B2* | 9/2016 | Stevens ........... A61M 25/10182 |
| 2002/0107565 | A1 | 8/2002 | Greenhalgh |
| 2007/0198097 | A1 | 8/2007 | Zegdi |
| 2009/0099517 | A1 | 4/2009 | Steadham |
| 2010/0010470 | A1 | 1/2010 | Bates |
| 2010/0116360 | A1 | 5/2010 | Kanner et al. |
| 2010/0121461 | A1 | 5/2010 | Sobrino-Serrano et al. |
| 2010/0168677 | A1 | 7/2010 | Gabriel et al. |
| 2011/0046604 | A1 | 2/2011 | Felsovalyi et al. |
| 2011/0190905 | A1 | 8/2011 | Behan |
| 2013/0116655 | A1 | 5/2013 | Bacino et al. |
| 2013/0123693 | A1 | 5/2013 | Lampropoulos et al. |
| 2014/0088498 | A1 | 3/2014 | Stevens et al. |
| 2014/0263403 | A1 | 9/2014 | Conner et al. |
| 2015/0051543 | A1* | 2/2015 | Chadwick ....... A61M 25/10182 604/97.02 |
| 2017/0246433 | A1* | 8/2017 | Kanner ........... A61M 25/10182 |
| 2018/0243540 | A1* | 8/2018 | Sykes ............. A61M 25/10184 |
| 2023/0079117 | A1* | 3/2023 | Beeby ................. A61M 5/3146 606/194 |
| 2024/0075259 | A1* | 3/2024 | Amine ............ A61M 25/10182 |

FOREIGN PATENT DOCUMENTS

| | | |
|---|---|---|
| JP | 04504072 | 7/1992 |
| JP | 2001523535 | 3/2003 |
| KR | 1020110025578 | 10/2011 |
| KR | 1020130047657 | 8/2013 |
| WO | 199011101 | 10/1990 |
| WO | 1999026692 | 6/1997 |
| WO | 199744077 | 11/1997 |
| WO | 2004058332 A2 | 7/2004 |
| WO | 2012154539 | 11/2012 |
| WO | 2015023923 | 2/2015 |
| WO | 2017147479 A1 | 8/2017 |

OTHER PUBLICATIONS

European Search Report dated Mar. 7, 2017 for EP14836509.1.
European Search Report dated Sep. 15, 2016 for EP12782669.1.
Extended European Search Report dated Jul. 15, 2015 for EP12782669.1.
International Search Report and Written Opinion dated Aug. 17, 2012 for PCT/US2012/036473.
International Search Report and Written Opinion dated Nov. 19, 2014 for PCT/US2014/051219.
Notice of Allowance dated Jan. 12, 2015 for U.S. Appl. No. 29/424,608.
Notice of Allowance dated Mar. 4, 2015 for U.S. Appl. No. 29/424,608.
Notice of Allowance dated Mar. 13, 2015 for U.S. Appl. No. 29/430,061.
Notice of Allowance dated Mar. 30, 2018 for U.S. Appl. No. 13/970,272.
Notice of Allowance dated Apr. 4, 2014 for U.S. Appl. No. 29/405,006.
Notice of Allowance dated Aug. 7, 2013 for U.S. Appl. No. 13/464,046.
Notice of Allowance dated Nov. 6, 2019 for U.S. Appl. No. 29/578,120.
Office Action dated Jan. 2, 2015 for U.S. Appl. No. 29/430,061.
Office Action dated Jan. 15, 2019 for U.S. Appl. No. 14/460,650.
Office Action dated Feb. 5, 2018 for U.S. Appl. No. 14/460,650.
Office Action dated Feb. 14, 2019 for U.S. Appl. No. 29/578,120.
Office Action dated Feb. 15, 2017 for U.S. Appl. No. 13/970,292.
Office Action dated Mar. 8, 2018 for U.S. Appl. No. 15/174,680.
Office Action dated Mar. 10, 2020 for U.S. Appl. No. 14/460,650.
Office Action dated Apr. 4, 2019 for U.S. Appl. No. 15/174,680.
Office Action dated Apr. 6, 2020 for U.S. Appl. No. 15/174,680.
Office Action dated Apr. 12, 2013 for U.S. Appl. No. 13/464,046.
Office Action dated Jul. 8, 2019 for U.S. Appl. No. 14/460,650.
Office Action dated Jul. 11, 2016 for U.S. Appl. No. 13/970,292.
Office Action dated Aug. 8, 2017 for U.S. Appl. No. 13/970,292.
Office Action dated Aug. 28, 2014 for U.S. Appl. No. 29/424,608.
Office Action dated Sep. 5, 2017 for U.S. Appl. No. 14/460,650.
Office Action dated Sep. 19, 2019 for U.S. Appl. No. 15/174,680.
Office Action dated Oct. 5, 2018 for U.S. Appl. No. 15/174,680.
Office Action dated Oct. 19, 2020 for U.S. Appl. No. 14/460,650.
Office Action dated Dec. 20, 2013 for U.S. Appl. No. 29/405,006.
International Search Report and Written Opinion dated Feb. 5, 2024 for PCT/US2023/075994.

* cited by examiner

HIGH PRESSURE INFLATION DEVICE

RELATED APPLICATIONS

This application claims priority to U.S. Provisional Application No. 63/378,429, filed on Oct. 5, 2022 and titled "High Pressure Inflation Device" which is hereby incorporated by reference in its entirety.

TECHNICAL FIELD

The present disclosure relates generally to devices used to pressurize, depressurize, or otherwise displace fluid, particularly in medical devices. More specifically, the present disclosure relates to high-pressure devices used to pressurize, depressurize, or otherwise displace fluid along a fluid line in order to inflate or deflate a medical device, such as a balloon. The disclosure further relates to features for avoiding overpressurization in such devices.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

DETAILED DESCRIPTION

Figure 1A:
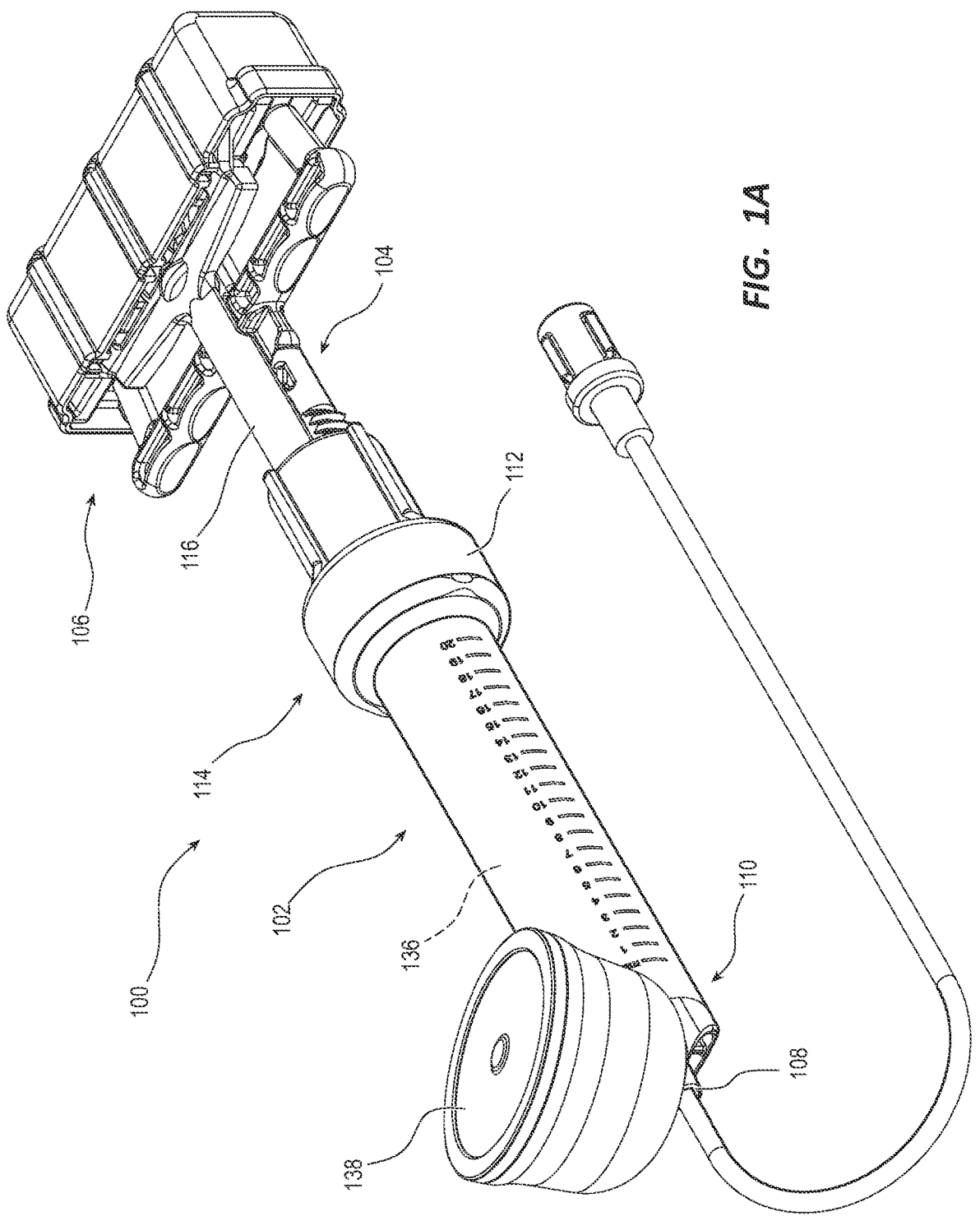
FIG. 1A is a front perspective view of an inflation device in accordance with an embodiment.

An inflation device may comprise a syringe which utilizes threads to advance or retract a plunger by rotating the plunger handle relative to the body of the syringe such that the threads cause longitudinal displacement of the plunger relative to the body. In some instances, an inflation syringe may comprise retractable threads, configured to enable a practitioner to disengage the threads and displace the plunger by simply pushing or pulling the plunger. The inflation syringe may comprise a coupling member configured to constrain movement of the plunger within the syringe body. The coupling member may comprise threads configured to engage with retractable threads.

Inflation devices within the scope of this disclosure may be used to generate relatively high pressures internally and within inflatable devices to which they are connected. In some cases, these pressures may exceed a rating of the inflation device and/or the inflatable device and thereby increase the possibility of failure. As described herein, such inflation devices may be configured to prevent excessively high pressures from being reached.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Further, various features are sometimes grouped together in a single embodiment, figure, or description thereof for the purpose of streamlining the disclosure. Many of these features may be used alone and/or in combination with one another.

The phrase "coupled to" refers to any form of interaction between two or more components, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device (or component thereof) means the end of the device/component furthest from the practitioner during use. The proximal end refers to the opposite end, or the end nearest the practitioner during use. As specifically applied to the syringe portion of an inflation device, the proximal end of the syringe refers to the end nearest the handle and the distal end refers to the opposite end, the end nearest the inlet/outlet port of the syringe. Thus, if at one or more points in a procedure a practitioner changes the orientation of a syringe, as used herein, the term "proximal end" always refers to the handle end of the syringe (even if the distal end is temporarily closer to the practitioner).

"Fluid" is used in its broadest sense, to refer to any fluid, including both liquids and gases as well as solutions, compounds, suspensions, etc., which generally behave as fluids.

FIGS. 1A-1E depict an embodiment of an inflation device 100 and related components. In certain views the device may be shown with components not included in every view. Further, in some views only selected components are illustrated, for example, to provide detail into the relationship of the components. Some components may be shown in multiple views, but not discussed in connection with every view.

Disclosure provided in connection with any figure is relevant and applicable to disclosure provided in connection with any other figure or embodiment.

Figure 1B:
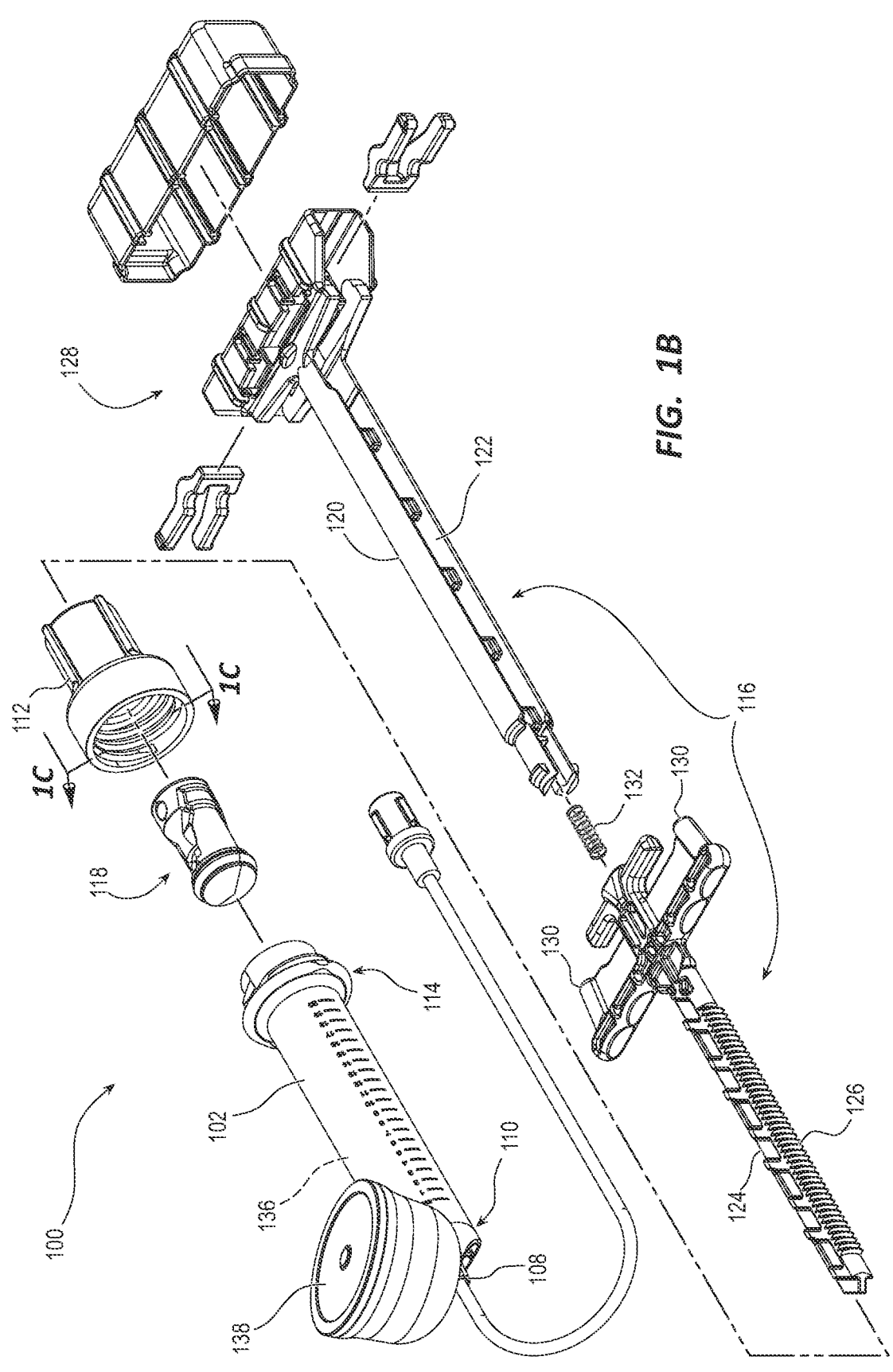
FIG. 1B is an exploded view of the inflation device of FIG. 1A.

With reference to the intact and exploded views of FIG. 1A and FIG. 1B respectively, the inflation device 100 may be described as comprising three broad groups of components; each of these groups may have multiple subcomponents and parts. The three broad component groups are: a body component such as a syringe body 102, a pressurization component such as a plunger 104, and a handle 106.

The syringe body 102 may be formed of a generally cylindrical hollow tube configured to receive the plunger 104. A nozzle 108 may be disposed at a distal end 110 of the syringe body 102. In some embodiments, a coupling member 112 may be coupled to the syringe body adjacent a proximal end 114 of the syringe body 102. The coupling member 112 may include a center aperture configured to allow the plunger 104 to pass through the coupling member 112 into the syringe body 102.

The plunger 104 may be configured to be longitudinally displaceable (i.e, configured for advancement and retraction) within the syringe body 102. The plunger 104 may comprise a shaft 116 coupled at a distal end thereof to a tip 118. The shaft 116 may also be coupled at a proximal end to a handle 106. The handle 106 broadly encompasses the group of components coupled to the proximal end of the plunger 104, some of which may be configured to be graspable by a user. In the illustrated embodiment, the shaft 116 and handle 106 each may comprise a group of components that interact to enable various modes of displacing the plunger 104 within the syringe body 102. In the illustrated embodiment, the shaft 116 can comprise: a thread guide 120 having a channel 122; and a thread rail 124 slidably disposed within the channel 122 and having a number of plunger threads 126 disposed thereon. As the plunger threads 126 are restricted to the thread rail 124, the plunger threads 126 do not extend 360 degrees around the axis of the plunger shaft 116. For example, in the illustrated embodiment, the plunger threads 126 may extend around the axis of the plunger shaft 116 less than 90 degrees. In other embodiments, the plunger threads 126 may extend around the axis of the plunger shaft 116 less than 80 degrees, less than 70 degrees, less than 60 degrees, less than 50 degrees, between about 30 degrees and 90 degrees, between about 30 degrees and 60 degrees, or between about 40 degrees and 50 degrees.

The handle 106 can comprise an actuator 128 coupled to the proximal end of the thread guide 120 and a trigger 130 coupled to the proximal end of the thread rail 124. The handle 106 can further include a biasing element 132 to provide a biasing force that may act, e.g., to hold the thread rail 124 in a particular position with respect to the channel.

A fluid reservoir 136 may be defined by the space enclosed by the inside walls of the syringe body between the plunger tip 118 and the distal end 110 of the syringe body 102. Accordingly, movement of the plunger tip 118 with respect to the syringe body 102 alters the size and volume of the fluid reservoir 136. In some instances, the plunger 104 may be displaced within the syringe body 102 such that fluid within the fluid reservoir 136 is compressed.

The nozzle 108 may be in fluid communication with the fluid reservoir 136. In some embodiments, the nozzle 108 is a male Luer fitting. A pressure gauge 138 can be coupled to the syringe body 102 such that the pressure gauge 138 is in fluid communication with the fluid reservoir 136. The pressure gauge 138 may be of any suitable type to measure a fluid pressure within the fluid reservoir 136. For example, the pressure gauge 138 can be an analog pressure gauge or a digital pressure gauge. Other types of pressure gauges are contemplated.

Figure 1C:
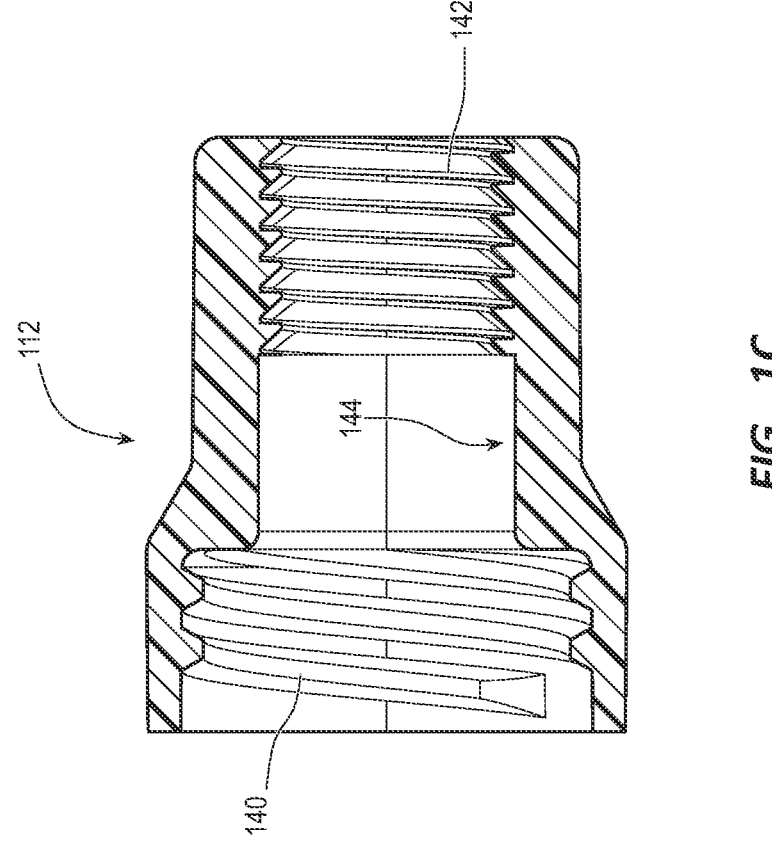
FIG. 1C is a longitudinal cross-section view of the coupling member of the inflation device of FIG. 1A taken at the plane indicated therein.
Figure 1D:
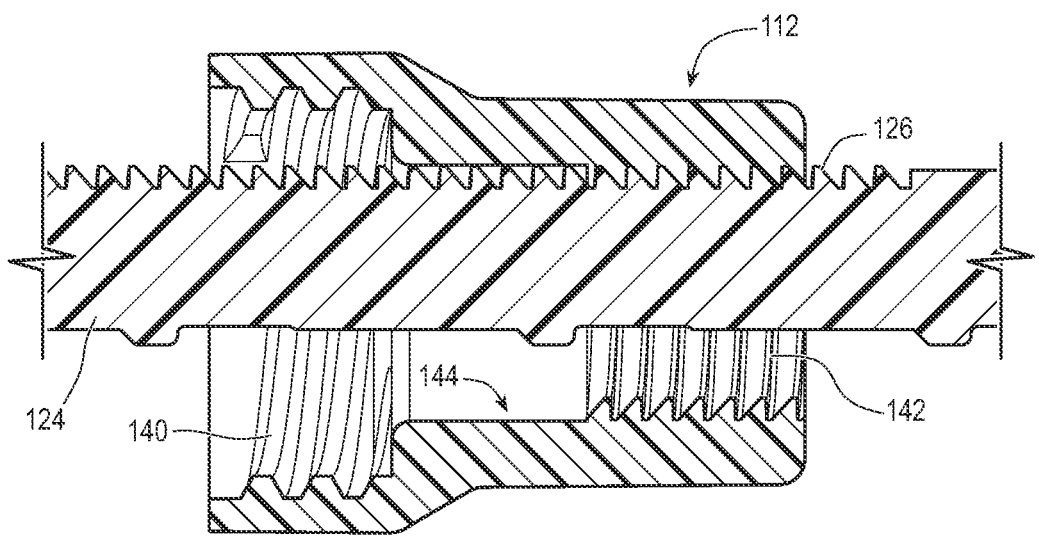
FIG. 1D is a longitudinal cross-section view of the coupling member of FIG. 1C in engagement with a plunger component of the inflation device of FIG. 1A.
Figure 1E:
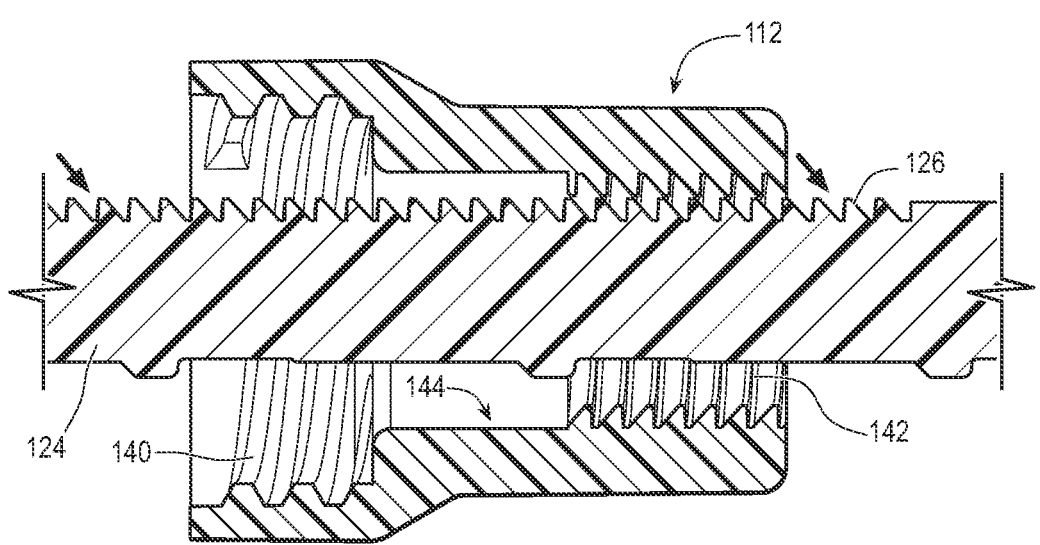
FIG. 1E is a longitudinal cross-section view of the coupling member and plunger component of FIG. 1D in a disengaged state.

As shown in the cross-section views of FIG. 1C through FIG. 1E, the coupling member 112 may include threads 140 or other coupling mechanisms to fixedly couple the coupling member 112 to the syringe body 102. The coupling member 112 may further include coupling member threads 142 formed on an inner surface 144 and configured to engage the plunger threads 126 as illustrated in FIG. 1D. As described above, the thread rail 124 on which the plunger threads 126 are situated is in turn situated within the channel of a thread guide (not shown in FIG. 1D and FIG. 1E). When the plunger threads 126 and coupling member threads 142 are engaged, the plunger 104 may be translated longitudinally with respect to the syringe body 102 by rotating the plunger 104 such that the interaction of the coupling member threads 142 and the plunger threads 126 results in the longitudinal translation of the plunger 104. Such rotating motion may be achieved when a user grasps and rotates the handle 106. As used herein, an "advancing direction" of rotation refers to a direction of rotation of the plunger 104 resulting in distal displacement of the plunger 104 when the threads 142, 126 are engaged. In some embodiments clockwise rotation may be configured to extend the plunger 104 distally and counterclockwise rotation may be configured to retract the plunger 104 proximally. Other embodiments may be configured with reverse threads configured to displace the plunger 104 distally when rotated counterclockwise and proximally when rotated clockwise.

The plunger 104 and handle 106 may be configured to allow retraction of the thread rail 124 into the thread guide 120. As illustrated in FIG. 1E, the thread rail 124 and thread guide 120 (not shown) can be configured to allow the thread rail 124 to move in a direction (e.g., as indicated by the arrow) that allows the plunger threads 126 to disengage from the coupling member threads 142. For example, the components of the plunger 104 and handle 106 can be configured so that a user can retract the thread rail 124 into the thread guide 120 by actuating the trigger 130. More specifically, when the trigger 130 is actuated with enough force to overcome the biasing force, the thread rail 124 and plunger threads 126 are permitted to separate from the inner surface 144 of the coupling member 112.

This functionality can facilitate certain modes of operation during use of the device. For example, in some instances, a practitioner may desire to quickly displace the plunger 104, for instance, while priming the inflation device 100 or while priming or deflating an attached medical device, such as a balloon. Quick displacement of the plunger 104 may be accomplished by retracting the plunger threads 126 and sliding the plunger 104 relative to the syringe body 102. For example, a practitioner may quickly fill the fluid reservoir 136 with fluid by disengaging the plunger threads 126 and pulling the plunger 104 in a proximal direction with respect to the syringe body 102. Further, a practitioner may quickly force fluid into lines leading to a medical device or quickly expel unwanted air bubbles from the fluid reservoir 136 by retracting the plunger threads 126 and repositioning the plunger 104. In other instances, for example when more precise control and/or mechanical advantage over displacement of the plunger 104 is desired, the practitioner may opt to displace the plunger 104 by rotation of the plunger 104 while the plunger threads 126 are engaged with the coupling member threads 142 as described above.

Fluid reservoir pressures can be increased by advancing the plunger 104 distally relative to the syringe body 102, particularly by rotating the plunger 104 in an advancing direction when the threads 142, 126 are engaged. Elevated reservoir pressures in turn can generate a number of reactionary forces on various components of the device. For example, pressure in the fluid reservoir 136 can produce a proximally directed axial force against the plunger tip 118, which may be translated from the plunger shaft 116 to the engaged surfaces of the plunger threads 126 and the coupling member threads 142. The resulting friction between the 126, 142 can make further advancement of the plunger via rotation more difficult, requiring the application of greater torque to the shaft 116, where "torque" herein refers to torque in a direction that would cause rotation of the shaft around its longitudinal axis. In some instances, the various forces generated on these components may exceed the material strength of one or more of the components, resulting in a catastrophic failure (i.e., damage that diminishes or eliminates the functionality of the inflation device 100). In various embodiments described herein, the inflation device 100 may include features to avoid catastrophic failure by providing one or more benign failure modes, (i.e., where the inflation device 100 "fails" to generate fluid reservoir 136 pressures that would make catastrophic failures likely). In particular embodiments, such benign failure modes can involve interruption of the functional connection between rotation of the plunger 104 and displacement of the plunger relative to the syringe body 102.

In the following discussion, overpressurization during use of an inflation device may be viewed with respect to a threshold pressure, i.e., a fluid reservoir pressure at or above which operation of the inflation device may result in a benign or designed failure to prevent catastrophic failure. Such a threshold pressure may be identified in relation to a tolerance or rating of the inflation device or a component thereof. In some embodiments, the threshold pressure is at or above a pressure rating of the inflation device. In some embodiments, the threshold pressure may be at or above a pressure rating of an inflatable device that the inflation device is configured to inflate. In some embodiments, the threshold pressure is about 600 psi to about 800 psi. In other embodiments the threshold pressure may be greater or smaller than this range, including embodiments from 450 psi to 900 psi, 500 psi to 800 psi, and so forth. Embodiments wherein the threshold pressure is at or slightly above the pressure rating, including embodiments where the threshold pressure is 50 psi, 100 psi, from 100 psi to 200 psi, from 10% to 50%, from 10% to 30%, from 10% to 20%, from 0% to 50%, or 0% to 20% higher than the pressure rating, as well as other ranges, are also within the scope of this disclosure. Pressure ratings from 300 psi to 600 psi, including from 300 psi to 500 psi, and 400 psi to 500 psi are also within the scope of this disclosure.

Features for avoiding overpressurization according to an embodiment can be seen in the views provided in FIG. 1C through FIG. 1E. As discussed above, the inner surface 144 of the coupling member 112 can include a number of coupling member threads 142 that can engage the plunger threads 126 to allow longitudinal displacement of the plunger 104 through rotation of the plunger 104. A number of forces can be considered to act on the engaged surfaces of the threads 126, 142, with some forces tending to maintain engagement ("engagement forces"), and other tending to cause disengagement ("disengagement forces"). For example, engagement forces may include a biasing force exerted by the biasing element 132, which may act to hold the thread rail 124 in a position so as to maintain engagement between the threads 126, 142. Friction between the engaged faces of the threads 126, 142 may also act to maintain engagement by resisting slip between these faces. On the other hand, pressure in the fluid reservoir 136 may exert a proximally directed force on the plunger 104, which may tend to promote proximally directed slippage of the plunger threads 126 past the coupling member threads 142.

The magnitude of the combined engagement forces may depend upon the total area of engaged thread surfaces. In the inflation devices described herein where the plunger threads are discrete rather than continuous, engaged thread surface area is a function of the number of coupling member thread turnings available for engagement with the plunger threads. As such, references to a number of coupling member threads or "thread number" in the following discussion are based on this value. Particular components of the engagement force (e.g., friction) may increase with thread number, thereby increasing the proximally directed force required to induce slippage or other disengagement of the threads 126, 142. As a result, with higher thread number, thread engagement— and therefore the capacity to increase fluid reservoir pressure by advancing the plunger through rotation—may persist until pressure is high enough to cause catastrophic failure. In some embodiments, the number of coupling member threads 142 is selected so that when a threshold pressure is reached, further rotation of the plunger 104 in an advancing direction causes the plunger threads 126 to disengage from the coupling member threads 142, thereby preventing further advancement of the plunger 104. Without being bound to a particular theory, disengagement at or above a threshold pressure corresponding to a particular thread number may be due to the engagement forces associated with the thread number being overcome by the disengagement force resulting from said pressure.

In one aspect, thread number may be stated in terms of the length of the inner surface 144, or fraction thereof, occupied by threads having a constant pitch. In another aspect, the number of coupling member threads 142 may be stated in terms of the total number of turns of the coupling member threads 142.

Figure 2A:
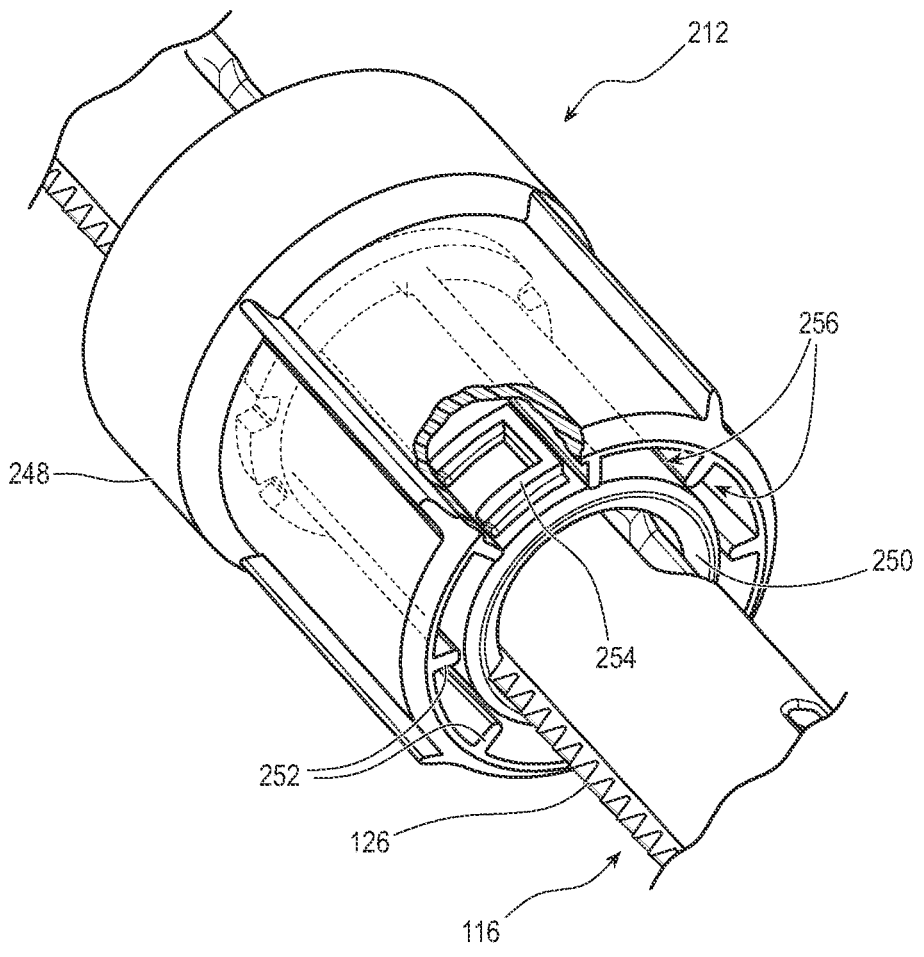
FIG. 2A is a perspective cutaway view of a coupling member and a plunger shaft of an inflation device in accordance with an embodiment.

In some embodiments, features for avoiding overpressurization may comprise mechanisms that limit the amount of torque applied to the plunger shaft that will produce advancement of the plunger. More particularly, at or above a threshold pressure the functional connection between rotation of the plunger shaft 116 and advancement of the plunger 104 relative to the syringe body 102 is interrupted. In one such embodiment, as illustrated in FIG. 2A, a coupling member 212 can comprise: a retainer ring 248 fixedly coupled to the syringe body 102; and a threaded insert 250 situated concentrically within the retainer ring 248. The threaded insert 250 can comprise coupling member threads 242 configured to engage plunger threads 126. The coupling member 212 may be configured so that the threaded insert 250 is capable of rotation within the retainer ring 248, but where free rotation of the threaded insert 250 is hindered during operation at fluid reservoir pressures below a threshold pressure. More particularly, the torque limiting mechanism can comprise features that function to resist rotation of the threaded insert 250 during rotation of the plunger shaft 116 over a range of operational pressures, so that torque applied to the plunger shaft 116 causes movement of the plunger threads 126 relative to the coupling member threads 242 and therefore produces longitudinal displacement of the plunger tip 118. Once a threshold torque is reached, such features may function to allow the threaded insert 250 to rotate with the plunger shaft 116, so that further application of torque does not produce displacement of the plunger tip 118.

Figure 2B:
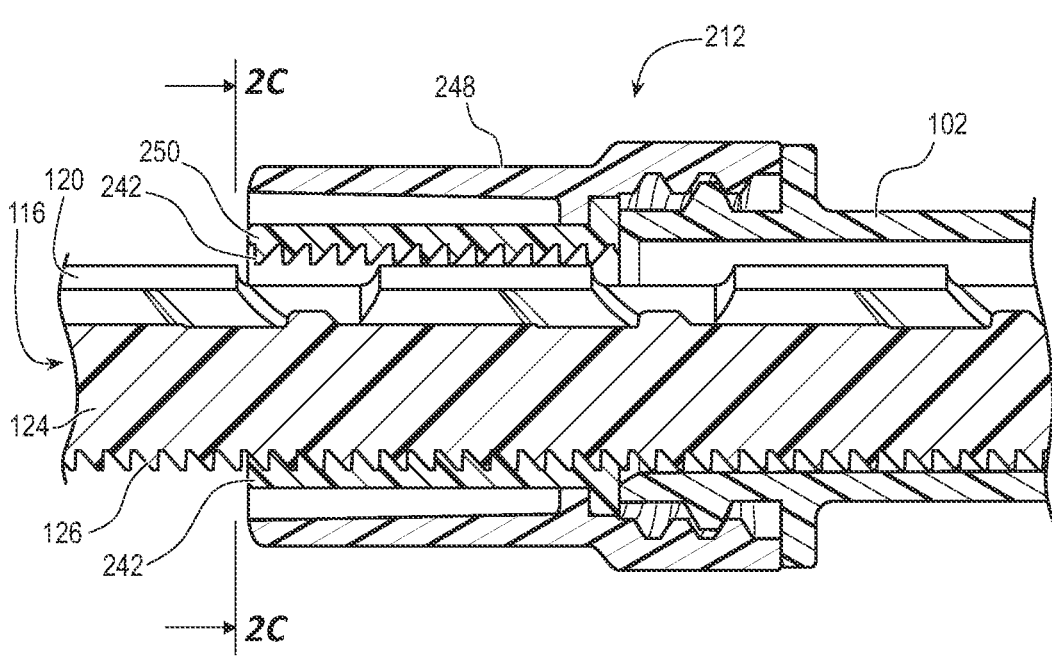
FIG. 2B is a longitudinal cross-section view of the components shown in FIG. 2A.
Figure 2C:
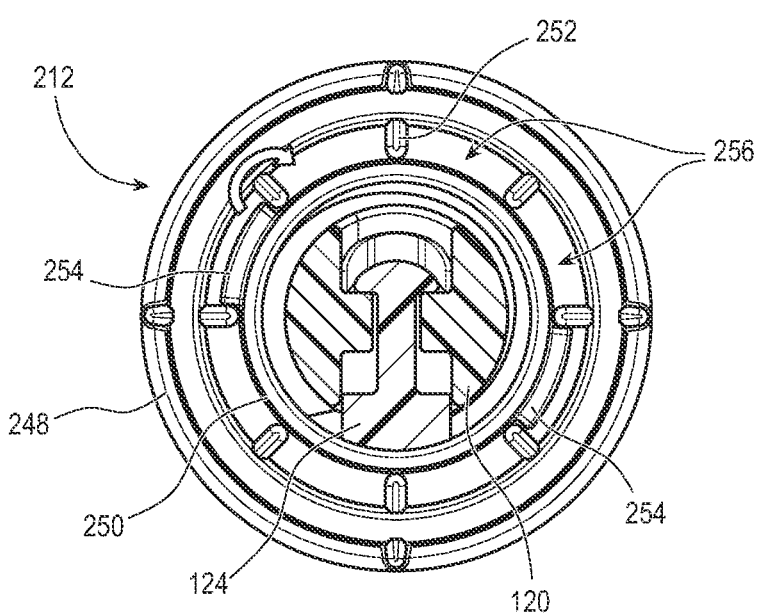
FIG. 2C is a cross section view of the components shown in FIG. 2A taken at the plane indicated in FIG. 2B.

In some embodiments, the retainer ring 248 can include inwardly-projecting retainer protrusions 252 and the threaded insert 250 can include one or more outwardly-projecting insert protrusions 254. The protrusions 252, 254 can be configured to interact with each other so as to interfere with rotation of the threaded insert 250 relative to the retainer ring 248. In some embodiments, one or both of the retainer protrusions and the insert protrusions can include longitudinally oriented ribs, for example, as illustrated in the embodiment shown in FIG. 2A through FIG. 2C.

As discussed above, the proximally directed force exerted on the plunger 104 by increasing fluid reservoir pressure may result in increased engagement between the plunger threads 126 and the coupling member threads 242. As pressure increases, more torque may be required to move the plunger threads 126 along the coupling member threads 242. Consequently, an increasing amount of torque is transmitted to the threaded insert 250, increasing its tendency to rotate. However, interaction between the insert protrusion 254 and the adjacent retainer protrusion 252 resists such rotation until the threshold pressure is reached, at which point further torque is sufficient to force the insert protrusion 254 to ratchet past the adjacent retainer protrusion 252. With joint rotation of the threaded insert 250 and the plunger shaft 116, no further advancement of the plunger tip 118 occurs due to the absence of relative movement between the threads 126, 242.

The ratcheting behavior of the torque limiting mechanism can be configured to prevent overpressurization by disrupting further pressurization under a suprathreshold torque condition, yet restore said function as soon as the condition ceases. This functionality may be better understood with reference to FIG. 2C, which shows a cross-section view taken at the plane indicated in FIG. 2B. As shown, a plurality of retainer protrusions 252 may be arranged so as to present a plurality of intervening windows 256 within which an insert protrusion 254 can rest during operation below the threshold pressure. Upon application of a suprathreshold torque to the plunger shaft 116, the insert protrusion 254 slips past an adjacent retainer protrusion 252 and comes to rest in the next window 256 and is contained therein. This action repeats until torque applied to the plunger shaft 116 is below the threshold, e.g., after depressurization of the fluid reservoir 136, whereupon the insert protrusion 254 remains within a window 256 and the threaded insert 250 remains stationary.

Interference between a retainer protrusion 252 and an insert protrusion 254 can be a product of spatial overlap between these elements. That is, the protrusions 252 and 254 may have a profile selected to produce a degree of overlap between the protrusions. As the degree of overlap increases, so may the interference with threaded insert 250 rotation also increase. Accordingly, in some embodiments, the magnitude of the threshold pressure may be determined at least in part by the degree of overlap. In various embodiments, material properties (e.g., stiffness) of the protrusions can also affect interference, in that ratcheting can involve deformation of one or both protrusions.

Figure 3:
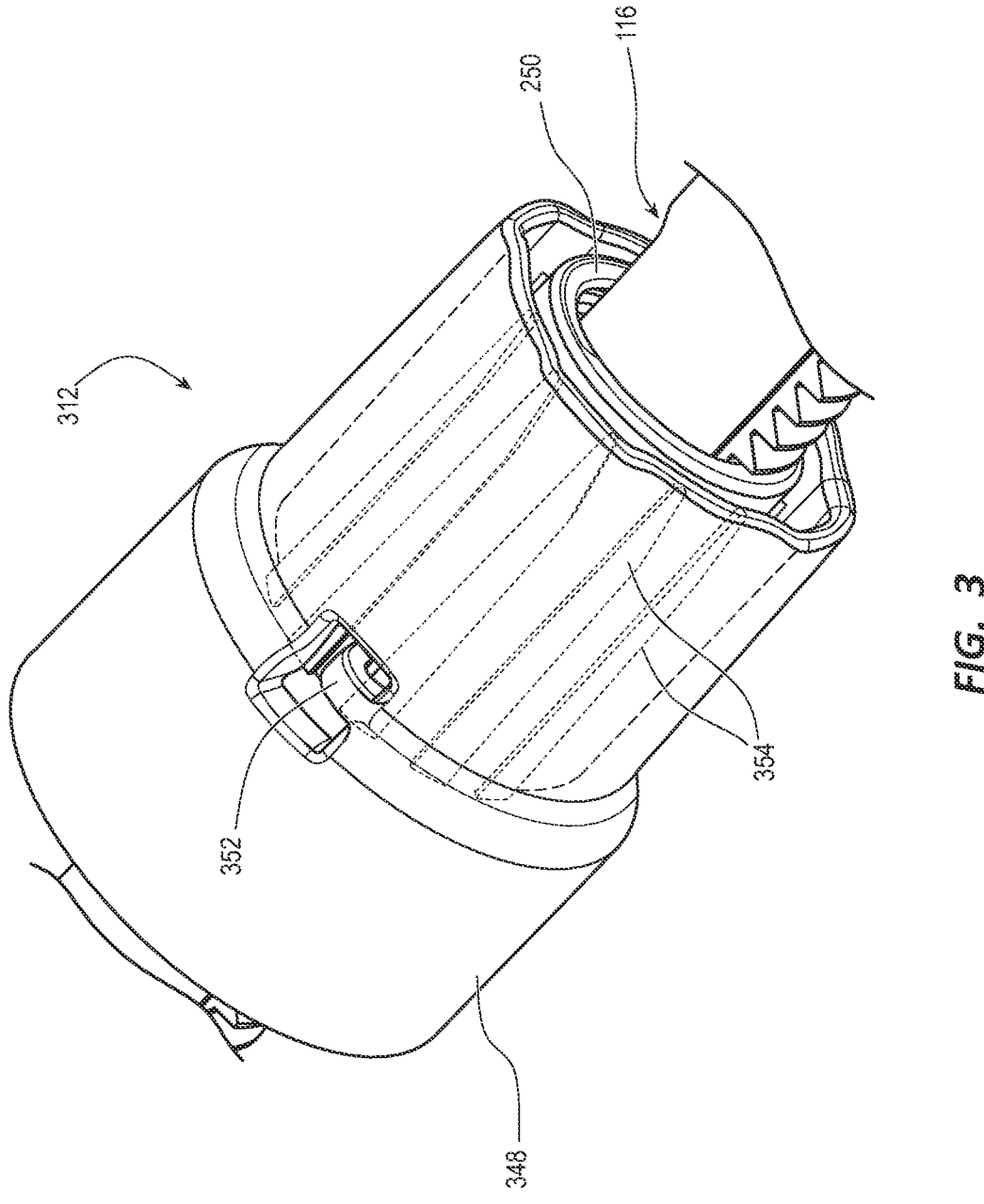
FIG. 3 is a perspective cutaway view of a coupling member and a plunger shaft of an inflation device in accordance with an embodiment.

A torque limiting mechanism according to another embodiment is illustrated in FIG. 3. As shown, a coupling member 312 can comprise a retainer ring 348 and a threaded insert 350 where the threaded insert 350 includes outwardly-projecting insert protrusions 354 and the retainer ring 348 includes one or more retainer protrusions 352 configured to interact with the insert protrusions 354. In the embodiment shown, the insert protrusions 354 comprise longitudinally oriented ribs, and the retainer protrusion 352 is a flexible hook positioned to interact with the ribs.

As discussed above with regard to the embodiment shown in FIG. 2A through FIG. 2C, the magnitude of the threshold pressure of the torque limiting mechanism illustrated in FIG. 3 may also be determined at least in part by the degree of overlap between the hook and the insert protrusions 354, by the material properties (e.g., flexibility) of the hook, or both.

As discussed above, the fluid reservoir 136 may be defined at least in part by the placement of the plunger tip 118 within the syringe body 102. Furthermore, pressure changes within the fluid reservoir 136 can be produced by movement of the plunger tip 118, which is accomplished through action on the handle 106 and shaft 116. Accordingly, inadvertent disconnection of the tip 118 from the shaft 116, e.g., due to negative pressures within the fluid reservoir or from an impact to the device, could result in a catastrophic failure of the device.

Figures 4A, 4B:
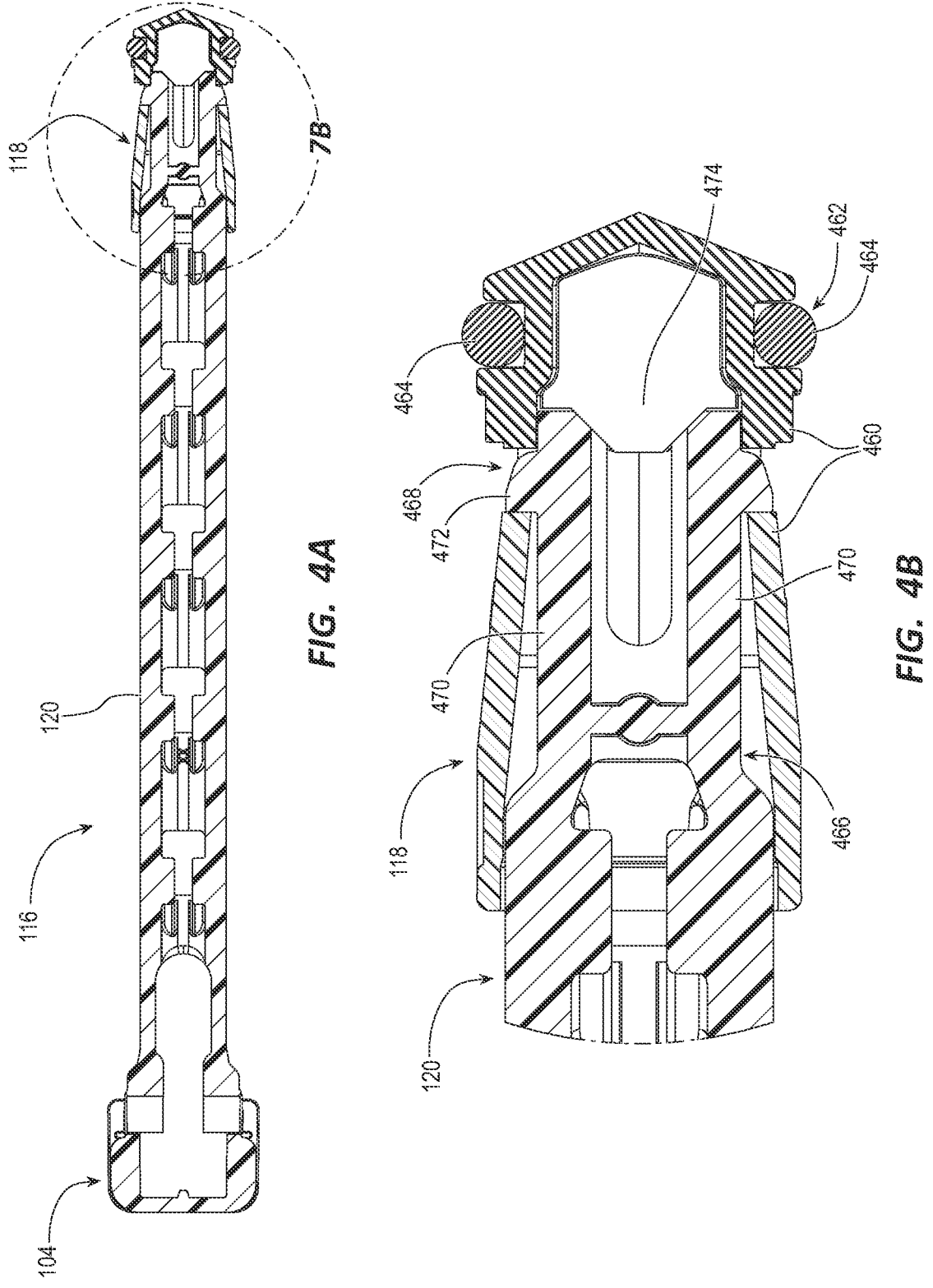
FIG. 4A is a longitudinal cross-section view of a plunger for an inflation device in accordance with an embodiment.
FIG. 4B is a detail view of the region of the plunger indicated by the circle in FIG. 4A.

FIG. 4A and FIG. 4B illustrate configuration of the plunger 104 for a secure connection between the tip 118 and the shaft 116. As shown in the cross-section view of FIG. 4A, the plunger shaft 116 includes the thread guide 120, onto the distal end of which the tip 118 is attached. Referring now to the magnified view shown in FIG. 4B, the plunger tip can include a tip body 460 having a generally cylindrical shape and at least a part of which may taper toward the distal end. The plunger tip body 460 may be formed of any suitable material, such as polycarbonate, high density polyethylene, polypropylene, acrylonitrile butadiene styrene, nylon, polyoxymethylene, polysulfone, polyetheretherketone, etc. In some embodiments, the materials may be reinforced or filled with a filler, such as glass. A circumferential channel 462 can be disposed adjacent a distal end. An O-ring 464 may be disposed within the channel to create a seal between the tip 118 and an interior surface of the fluid reservoir. The tip body 460 can include a bore that is open at a proximal end and closed at the distal end, where the bore is configured to receive the flexible legs 470. One or more notches 468 may extend outwardly from the bore into the wall of the tip body 460. In some embodiments, the notches may completely penetrate the tip body 460.

The distal end of the thread rail 124 can comprise a plurality of flexible legs 470. The flex arms may be separated by a plurality of slots, where said slots allow the flexible legs 470 to bend inwardly and outwardly to a slight degree. The flexible legs 470 may each include an outwardly-extending barb 472.

The diameter of the thread rail 124 at the level of the barbs 472 relative to the tapered region of the bore 466 may be such that insertion of the distal end of the thread rail 124 into the bore 466 causes inward bending of the flexible legs 470. As the distal end of the thread rail proceeds into the bore 466 and the barbs 472 align with the notches 468, spring action by the flexible legs 470 pushes the barbs 472 into the notches 468. The barbs 472 may be shaped to resist movement of the thread rail 124 relative to the tip body 460, particularly movement in the proximal direction.

As shown in FIG. 4B these components may comprise additional features to strengthen the interaction between the barbs 472 and the notches 468. For example, the tip body 460 may include a spreader element situated within the bore and configured so that, as the flexible legs 470 are inserted far enough into the bore 466 to encounter the spreader element, the spreader element spreads the flexible legs 470 outward. As illustrated in FIG. 4B, in some embodiments the thread rail 124 includes a pair of opposing flexible legs 470 and a spreader rib 474 extends across the distal end of the bore 466, where the spreader rib 474 is oriented so that the flexible legs 470 pass on opposite sides of the spreader rib 474 during insertion. The spreader rib 474 can have a cross-sectional profile that promotes increased spreading of the flexible legs 470 as insertion proceeds. In certain embodiments, the rib has a trapezoidal profile.

In some embodiments, the notches 468 are situated relative to the spreader element so that spreading of the flexible legs 470 commences before the barbs 472 reach the notches 468. As a result, upon reaching the notches 468 the barbs 472 are forcefully pushed into the notches and held there securely. In some embodiments, the dimensions of the components, e.g., the thickness of the flexible legs 470 and/or the gap between the spreader element and the notches 468, may be selected so that deformation (e.g., compression) of the flexible legs 470 occurs during the above assembly process. A certain amount of force may therefore be needed to insert the plunger shaft 116 far enough into the tip body 460 to accomplish a secure connection. In certain embodiments, the force needed is at least about 100 lbs, or in some instances, about 100 lbs to about 200 lbs.

As discussed above and as shown in FIG. 4A and FIG. 4B an O-ring 464 may be disposed within the channel to create a fluidtight seal between the tip 118 and an interior surface of the fluid reservoir. The O-ring 464 may comprise an elastomeric material suited for such purposes. Under some conditions, an O-ring 464 comprising certain elastomeric materials may adhere to the fluid reservoir interior surface. Such elastomeric materials include ethylene propylene diene monomer rubber and other high compression set elastomers. Such adhesion may be strong enough that the application of considerable force, for example about 30 lbs, may be required to break the adhesion and change the position of the plunger. Such conditions can include exposure to heat and humidity, such as during storage, transport, or sterilization of the inflation device. In some embodiments, the O-ring 464 can comprise an elastomeric material that exhibits less adhesion under such conditions. More particularly, the O-ring 464 comprising this elastomeric material exhibits a level of adhesion to the fluid reservoir interior surface that requires less than about 10 lbs, or about 5 lbs to about 8 lbs of force to break. In certain embodiments, the O-ring 464 comprises silicone rubber.

Figure 5:
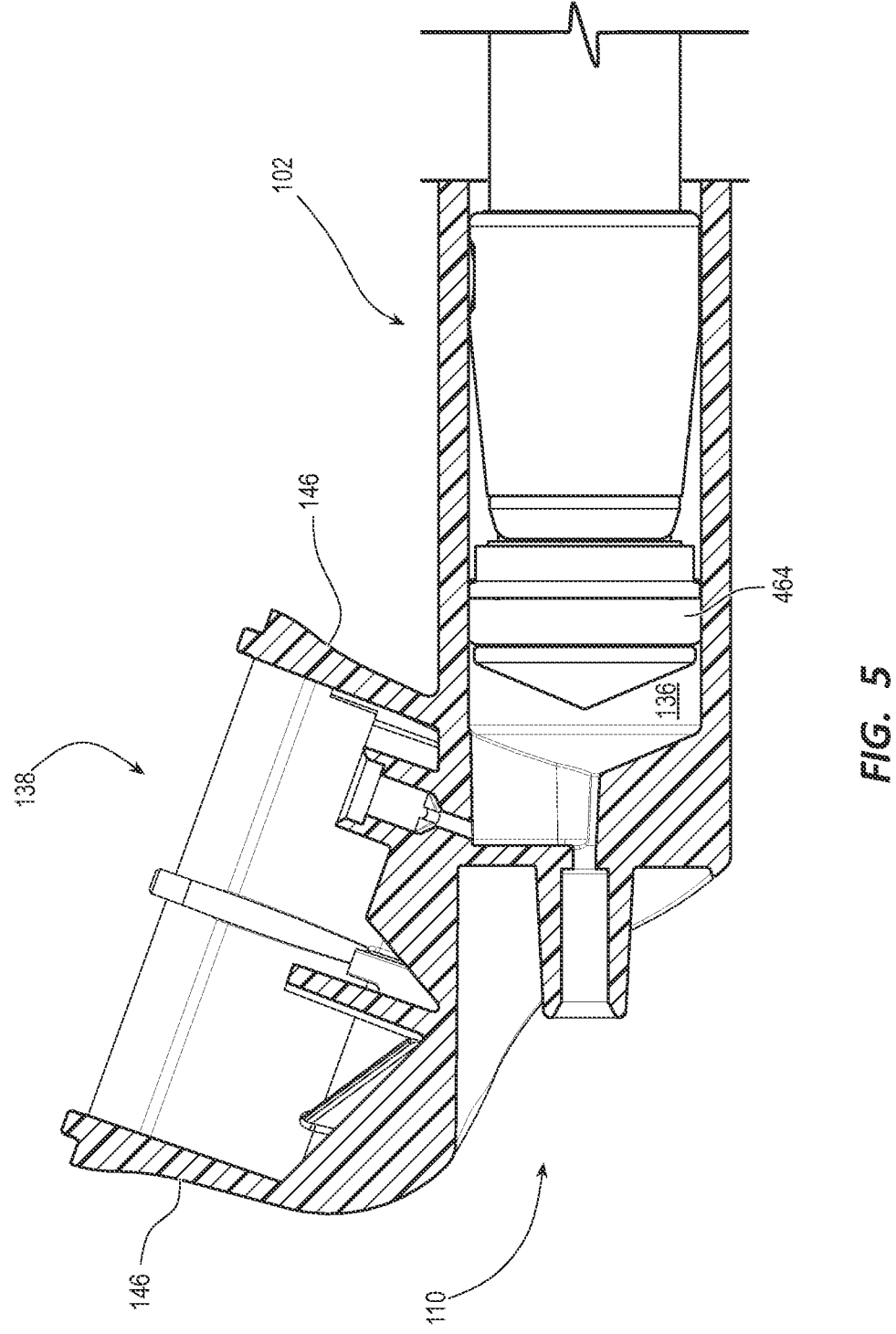
FIG. 5 is a longitudinal cross-section view of a selected portion of an inflation device in accordance with an embodiment.

FIG. 5 shows an enlarged cross-section view of the distal end 110 of the inflation device 100 shown in FIG. 1A and FIG. 1B. The inflation device 100 can include a pressure gauge 138 located in a housing 146 situated at the distal end 110 of the syringe body 102. The pressure gauge 138 can be in fluid communication with the fluid reservoir 136. In some embodiments, the housing 146 and the syringe body 102 may be constructed of a single piece of material. For example, the housing 146 and syringe body 102 may be part of a single piece of molded plastic. As part of the molding process, shrinkage can occur as the plastic cools and solidifies. In some cases, various sections of the molded piece may shrink to differing degrees and in different directions. This may result in deformation that affects device function. In a particular case, shrinkage among various regions of the syringe body 102, particularly the housing 146 and the distal regions of the fluid reservoir 136, may result in deformation of the fluid reservoir 136. Nonlinearity in the interior surface of the fluid reservoir 136 can reduce the ability to preserve a fluidtight seal between the O-ring 464 and the interior surface. In some embodiments, the syringe body 102 is constructed so that the interior surface of the fluid reservoir 136 contacted by the O-ring 464 is substantially uniform. More particularly, the housing 146 may be situated distal of the fluid reservoir 136 as illustrated in FIG. 5. In a particular embodiment, the housing is situated substantially distal of the most distal point in the fluid reservoir 136 reachable by the O-ring 464.

Figure 6:
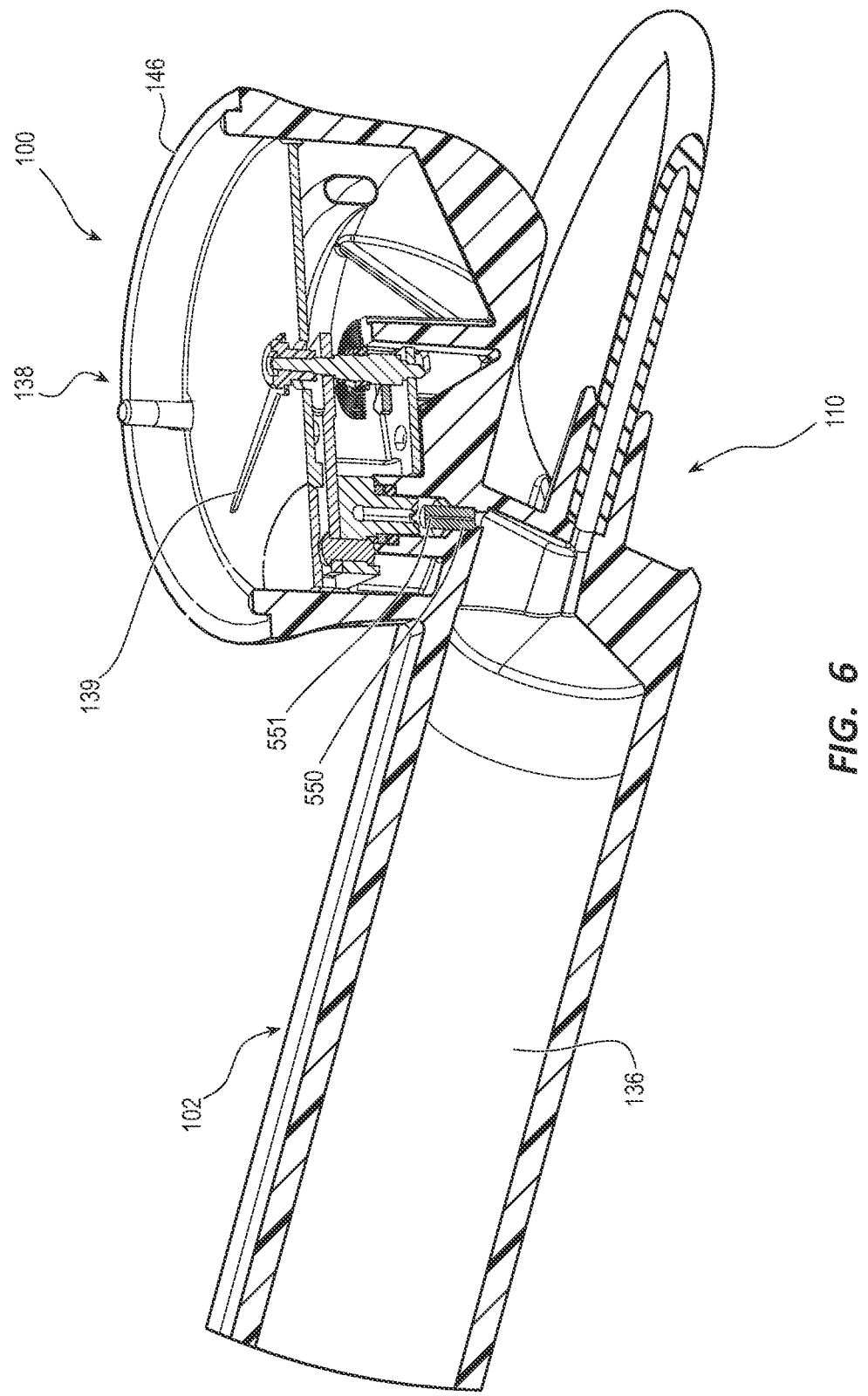
FIG. 6 is a longitudinal cross-section view of a selected portion of an inflation device in accordance with another embodiment.

FIG. 6 shows an enlarged cross-section view of the distal end 110 of the inflation device 100 shown in FIG. 1A and FIG. 1B. The inflation device 100 can include an orifice restrictor 550 located in the housing 146 situated at the distal end 110 of the syringe body 102. The orifice restrictor 550 can be in fluid communication with the pressure gauge 138 and with the fluid reservoir 136. As illustrated in FIG. 6, the orifice restrictor 550 includes a bore 551 extending longitudinally through the orifice restrictor 550. The bore 551 may have a diameter ranging from about 0.15 millimeter to about 0.35 millimeter, including from about 0.2 mm to about 0.3 mm. The orifice restrictor 550 may be formed from any suitable material using a thermal extrusion process. For example, the orifice restrictor 550 may be formed from a rigid nylon material. Other suitable materials are within the scope of the disclosure. The orifice restrictor 550 can be assembled to the housing 146 using any suitable method, such as press fit, gluing, bonding, welding, etc. Other suitable methods are within the scope of the disclosure. Additionally, though there are advantages to use of a thermal extrusion process for form the orifice restrictor, in other embodiments, the orifice restrictor may be formed by other processes, such as machining or laser cutting.

In use, the orifice restrictor 550 can dampen a pressure change applied to the pressure gauge 138 to prevent damage to the pressure gauge 138. In other words, the orifice restrictor 550 can lengthen a time required for fluid pressure to equalize on a pressure gauge side of the orifice restrictor 550 and on the fluid reservoir side of the orifice restrictor 550. For example, when the inflation device 100 is pressurized and then quickly depressurized through disengagement of the coupling member threads 142 and the plunger threads 126, as previously described, the fluid pressure within the fluid reservoir 136 may drop to below zero pounds per square inch within about five milliseconds. Without the orifice restrictor 550 disposed between the fluid reservoir 136 and the pressure gauge 138, the fluid pressure on the pressure gauge 138 may also drop to below zero pounds per square inch within about five milliseconds causing a pressure indicator needle 139 of the pressure gauge 138 to be suddenly displaced and forced against a hard stop of the pressure gauge 138. This may damage the pressure gauge 138 resulting in inaccurate subsequent pressure readings of the pressure gauge 138. When the orifice restrictor 550 is disposed within the housing 146, the time required for fluid pressure equalization may range from about 100 milliseconds to about 200 milliseconds avoiding damage to the pressure gauge 138.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments the feature can have a precisely perpendicular configuration.

The terms "a" and "an" can be described as one, but not limited to one. For example, although the disclosure may recite a plunger tip having "an O-ring," the disclosure also contemplates that the plunger tip can have two or more O-rings.

Unless otherwise stated, all ranges include both endpoints and all numbers between the endpoints.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

What is claimed is:

1. An inflation device, comprising:
a syringe body;
a plunger comprising a plunger shaft and a plunger tip and configured for advancement and retraction within the syringe body;
a fluid reservoir defined by an interior surface of the syringe body and the plunger tip;
plunger threads disposed on the plunger; and
a coupling member having an inner surface within which a number of coupling member threads are disposed, wherein said coupling member threads are configured to engage the plunger threads,
wherein the number is selected so that rotation of the plunger in a direction relative to the coupling member advances the plunger within the syringe body through engagement of the coupling member threads and the plunger threads, and increases a pressure within the fluid reservoir until a threshold pressure is reached, and
wherein when the threshold pressure is reached, further rotation of the plunger in said direction causes disengagement of the plunger threads from the coupling member threads, preventing further advancement of the plunger.

2. The inflation device of claim 1, wherein the disengagement is caused by one or more disengagement forces exerted on the plunger at fluid reservoir pressures at or above the threshold pressure.

3. The inflation device of claim 2, wherein the disengagement forces include an axial force exerted on the plunger tip.

4. The inflation device of claim 1, wherein the threshold pressure is about 600 psi to about 800 psi.

5. The inflation device of claim 1, wherein the threshold pressure is at or above a pressure rating of the inflation device.

6. The inflation device of claim 1, wherein the threshold pressure is at or above a pressure rating of an inflatable device to be inflated by the inflation device.

7. The inflation device of claim 1, further comprising an O-ring provided in a circumferential channel of the plunger tip, said O-ring comprising an elastomeric material that resists adhesion to the interior surface of the syringe body.

8. The inflation device of claim 1, further comprising a pressure gauge in fluid communication with the fluid reservoir to measure the pressure within the fluid reservoir,
wherein the pressure gauge is at least partially enclosed within a housing integrated into the syringe body, and
wherein the housing is situated substantially distal of the fluid reservoir.

9. The inflation device of claim 8, wherein the housing includes an orifice restrictor in fluid communication with the pressure gauge and the fluid reservoir,
wherein the orifice restrictor comprises a bore extending therethrough having a diameter ranging from 0.2 millimeter to 0.3 millimeter.

10. An inflation device, comprising:
a syringe body;
a plunger comprising a plunger shaft and a plunger tip and configured for advancement and retraction within the syringe body;
a fluid reservoir defined by an interior surface of the syringe body and the plunger tip;
plunger threads disposed on the plunger;
a coupling member surrounding the plunger shaft and comprising:
a retainer ring fixedly coupled to the syringe body;
a threaded insert situated concentrically within the retainer ring and having an inner surface comprising coupling member threads configured to engage the plunger threads; and
a torque limiting mechanism configured to hold the threaded insert stationary when a torque applied to the plunger shaft is below a threshold value, and to allow the threaded insert to rotate with the plunger shaft when the torque equals or exceeds the threshold value,
wherein rotation of the plunger when the threaded insert is stationary advances the plunger within the syringe body through engagement of the coupling member threads and the plunger threads, and increases a pressure within the fluid reservoir.

11. The inflation device of claim 10, wherein the threshold value is a torque at which advancement of the plunger increases the pressure within the fluid reservoir to a threshold pressure.

12. The inflation device of claim 10, wherein the torque limiting mechanism comprises:
one or more inwardly-projecting retainer protrusions disposed on a surface of the retainer ring; and
one or more outwardly-projecting insert protrusions disposed on the threaded insert,
wherein the retainer protrusions and the insert protrusions are configured to mutually interfere to resist rotation of the threaded insert relative to the retainer ring so that such rotation is prevented when the torque applied to the plunger shaft is below the threshold value.

13. The inflation device of claim 12, wherein one or both of the retainer protrusions and insert protrusions include longitudinally oriented ribs.

14. The inflation device of claim 12, wherein the one or more retainer protrusions comprise a flexible hook.

15. The inflation device of claim 12, wherein a plurality of the retainer protrusions are arranged so as to be separated by windows within which one of the insert protrusions is contained when the torque applied to the plunger shaft is below the threshold value.

16. The inflation device of claim 12, comprising a spatial overlap between the retainer protrusions and the insert protrusions selected to prevent rotation of the threaded insert relative to the retainer ring when the torque applied to the plunger shaft is below the threshold value.

17. A plunger for adjusting pressure in an inflation device, comprising:

a plunger shaft having a distal end comprising a plurality of distally extending flex arms radially arranged around a longitudinal axis of the plunger shaft, wherein each flex arm includes a barb extending radially therefrom;

a plunger tip configured to be secured to the distal end of the plunger shaft, said plunger tip comprising:

a tip body encompassing a bore configured to receive the distal end of the plunger shaft;

a plurality of notches extending radially from the bore and configured to admit and retain the barbs when the flex arms are fully inserted within the bore;

a spreader element situated in a distal end of the bore, configured to spread the flex arms when the flex arms are inserted within the bore to secure the barbs in the notches.

18. The plunger of claim 17, wherein the plunger shaft comprises two flex arms, and the spreader element is a rib oriented so that the flex arms each pass on opposite sides of the rib during insertion.

19. The plunger of claim 18, wherein at least one of the flex arms has a thickness relative to a gap between the spreader element and one of the notches such that deformation of the flex arm occurs before the barb enters the notch.

20. The plunger of claim 17, further comprising an O-ring provided in a circumferential channel of the tip body, said O-ring comprising silicone rubber.

* * * * *